US011151223B1

(12) United States Patent
Lee et al.

(10) Patent No.: US 11,151,223 B1
(45) Date of Patent: Oct. 19, 2021

(54) SYSTEM FOR LIFE-CYCLE TRACKING OF THERAPEUTIC DRUGS

(71) Applicant: Zyno Medical, LLC, Natick, MA (US)

(72) Inventors: Chao Young Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 351 days.

(21) Appl. No.: 15/241,399

(22) Filed: Aug. 19, 2016

Related U.S. Application Data

(60) Provisional application No. 62/207,664, filed on Aug. 20, 2015.

(51) Int. Cl.
G06F 19/00 (2018.01)
G08B 21/18 (2006.01)
G16H 15/00 (2018.01)
G16H 10/60 (2018.01)

(52) U.S. Cl.
CPC ......... G06F 19/3456 (2013.01); G08B 21/18 (2013.01); G16H 10/60 (2018.01); G16H 15/00 (2018.01)

(58) Field of Classification Search
None
See application file for complete search history.

(56) References Cited

U.S. PATENT DOCUMENTS

| 8,652,093 | B2 | 2/2014 | Lee et al. | |
|---|---|---|---|---|
| 8,945,043 | B2 | 2/2015 | Lee et al. | |
| 9,378,334 | B2 | 6/2016 | Lee et al. | |
| 2004/0172283 | A1* | 9/2004 | Vanderveen | G06F 19/325 705/2 |
| 2006/0047538 | A1* | 3/2006 | Condurso | G06F 19/326 705/3 |
| 2006/0200369 | A1* | 9/2006 | Batch | A61M 5/16827 705/3 |
| 2009/0210252 | A1* | 8/2009 | Silver | G06Q 10/10 705/3 |
| 2011/0119612 | A1* | 5/2011 | Gannon | G06F 3/0481 715/771 |
| 2013/0018356 | A1* | 1/2013 | Prince | G06Q 50/24 604/506 |
| 2014/0194817 | A1 | 7/2014 | Lee et al. | |
| 2014/0216978 | A1* | 8/2014 | Brahm | G09F 3/0292 206/534 |
| 2014/0350950 | A1* | 11/2014 | Jaskela | G06F 19/3456 705/2 |
| 2015/0165118 | A1 | 6/2015 | Lee et al. | |
| 2018/0114598 | A1* | 4/2018 | Kolberg | G16H 10/60 |

* cited by examiner

Primary Examiner — Jan P Mincarelli
(74) Attorney, Agent, or Firm — Boyle Fredrickson S.C.

(57) ABSTRACT

A system for lifecycle tracking of drugs provides for medical pumps to provide end of delivery cycle recording of the disposition of drugs, both for drugs that are administered by pump and those administered manually. By introducing drug dispensing identification upstream, for example, at the pharmacy, the invention allows automatic recording of the drug delivery by medical pumps communicating with the central server system. The result is a lifecycle manifest having records linked to a patient that identifies the travel of the drug and delivery of the drug through the medical care system from pharmacy to patient, and identifies discrepancies in drug utilization.

20 Claims, 5 Drawing Sheets

| ORDER ID ~73 | DRUG ID ~83 | PATIENT NAME ~88 | DRUG DOSE ~89 | DISPENSED ~86 | ADMINISTERED ~114 | AMT DELIVERED ~118 | UTILIZATION RATE ~120 | INTERRUPTION ~122 | STATUS ~116 | NOTES ~78 |
|---|---|---|---|---|---|---|---|---|---|---|
| - | - | - | | PENDING | | | | | ON ORDER | |
| - | - | - | 1L | 1/5/21 | 1/5/21 | 1L | 100% | NO | COMPLETE | |
| - | - | - | | 1/7/21 | EXPIRED | | | | UNACCOUNTED | |
| - | - | - | | URGENT | | | | | URGENT | |
| - | - | - | 1L | 1/6/21 | 1/7/21 | 500 mL | 50% | YES | INCOMPLETE | |

69 ─

130 ─

| DRUG RETURN | AMT RETURNED |
|---|---|
| 1/5/21 | 0 |
| 1/7/21 | 500 mL |

REPORT FOR DR. _____

CONTROLLED SUBSTANCE

| ORDER ID | DRUG ID | UTILIZATION RATE | NOTES |
|---|---|---|---|
| — | — | 100% | |
| — | — | 100% | |
| — | — | 80% | |
| — | — | 90% | |
| AVG. UTILIZATION RATE | | 92.5% | |

UNCONTROLLED SUBSTANCE

| ORDER ID | DRUG ID | UTILIZATION RATE | NOTES |
|---|---|---|---|
| — | — | 100% | |
| — | — | 100% | |
| — | — | 100% | |
| AVG. UTILIZATION RATE | | 100% | |

FIG. 7

SYSTEM FOR LIFE-CYCLE TRACKING OF THERAPEUTIC DRUGS

CROSS-REFERENCE TO RELATED APPLICATION

This application claims the benefit of U.S. provisional application 62/207,664 filed Aug. 20, 2015 and hereby incorporated by reference.

BACKGROUND OF THE INVENTION

The present invention relates to systems for the delivery of medicines to patients and in particular to a system to complete a comprehensive lifecycle tracking of therapeutic drugs and/or fluids.

Therapeutic drugs/fluids are an important part of healthcare but can be a significant cost in the provision of medical care, for example, in a hospital environment. In the process of healthcare delivery, drug orders can be duplicated, wasted, or lost. Drugs can be administered with inaccurate, or even dangerous parameters, to the wrong patient, through a wrong route, etc. In many situations, for example, in the operating room it may be difficult to capture drug administration events that allow tracking of drug usage. Some drugs once they are dispensed or compounded may have a limited shelf life before they must be administered or should be discarded. Loss of drugs through expiration and duplicate orders can be difficult to track or control. While good records often exist with respect to the dispensing and administering of drugs, determining the ultimate disposition of the drugs and hence the lifecycle use of the drug is difficult.

SUMMARY OF THE INVENTION

The present invention provides improved lifecycle tracking of drugs to reduce medical error and/or drug waste and loss by encoding all drug packages with tracking information and enlisting devices such as medical pumps to provide end of delivery cycle recording of the disposition of drugs, both for drugs that are administered by pump and those administered manually. By introducing a unique drug dispensing identification number upstream to drug packages, for example, at the pharmacy, the invention allows automatic recording of the drug administration by infusion or other medical pump communicating with the central server system. The result is a lifecycle manifest having records linked to a patient that identifies the travel of the drug and administering of the drug through the medical care system from pharmacy to patient.

At the pharmacy, the admixture preparation device may query the server to obtain patient context and/or order context for the preparation of the admixture to be administered by a downstream administration device. The admixture preparation device is able to document the admixture preparation details such as exactly how much a single or multiple component being mixed into the final admixture; send the admixture preparation details in the server; generate an identifier to be placed with the admixture to enable the downstream medication administration device to query the same server to retrieve the admixture preparation information as context for delivery.

Information can be carried by a data carrier (such as a readable label, barcode, a RFID tag, etc.), which may contain private information not to be readily accessible by unauthorized party. With the identifier generated by the admixture preparation device, the admixture details information along with the patient and/or order information is stored at the server, or a portion of the private information of the admixture preparation process is stored at the server so only the authorized party is able to request the access of the information.

The admixture preparation device may be a computer which documents the process of the admixture preparation process or, a device with a computer to draw ingredients of the admixture out of storage containers equipped with automatic dispensing or measuring mechanisms and physically mix the ingredients into the admixture. The admixture preparation device may be able to provide detailed instructions for mixing/packaging of drug(s) based on the patient and/or order context provided by the server.

One embodiment of the present invention provides a system for tracking delivery of medicine in a drug delivery container having a dispensing terminal for receiving information from an individual dispensing drugs to create a dispensing order indicating the drug identity and a drug dose for transmission to a pump; at least one pump receiving the dispensing order to deliver a drug to a patient according to the dispensing order and to transmit a completion order identifying the drug delivered to the patient and an amount of drugs delivered to the patient; and a tracking computer communicating with the dispensing terminals and pump and executing a program fixed in a non-transitory media to: (a) receive the dispensing order for a given drug; (b) receive the completion order for the given drug; (c) match the completion order to the dispensing order to determine utilization of the given drug providing a comparison between an amount of drug dispensed as indicated by the dispensing order and an amount of drug consumed as indicated by the completion order; and (d) output a lifecycle report indicating drug utilization.

It is thus a feature of at least one embodiment of the invention to track drug utilization from pharmacy to patient and to better assure drugs are properly administered and to help track and manage possible waste.

The tracking computer produces an alert when the utilization is below a predetermined threshold value.

It is thus a feature of at least one embodiment of the invention to automatically identify situations where additional attention to managing waste or misuse may be required.

The dispensing order may also include a physician identification and the tracking computer may output a physician report indicating drug utilization on a physician basis.

It is thus a feature of at least one embodiment of the invention to provide information that may permit a physician to compare their practice with those of their peers with respect to reducing drug waste and or to identify possible loss channels The pump may transmit a drug interruption status and the tracking computer may produce an alert when the drug delivery is interrupted.

It is thus a feature of at least one embodiment of the invention to track information relevant to possible diversion of drugs.

The pump may provide a data carrier reader that receives a drug identification from a drug container tag to match the drug identification with the dispensing order. The data carrier reader receives a patient identification from a patient data carrier such as a readable label, barcode, or a RFID tag on a wrist tag on the patient to match the patient identification with the dispensing order. Operation of the pump is allowed only if patient and drug information entered into the pump is consistent with the dispensing order. The drug container tag may be tamper resistant.

It is thus a feature of at least one embodiment of the invention to reliably report a drug identity and patient identity at the pump preventing individuals from inputting a false drug or patient identity.

The pump transmits a date of delivery of the given drug and the tracking computer communicating with the pump receives the date of delivery date and outputs the lifecycle report indicating a date of delivery of the given drug.

It is thus a feature of at least one embodiment of the invention to keep track of drug delivery efficiencies and sort drug orders by date to eliminate long waits between dispensing and delivery.

The dispensing order includes a drug expiration date and the tracking computer matches the expiration date with a date at the start of drug delivery to determine a drug expiration status.

It is thus a feature of at least one embodiment of the invention to reduce instances of drug expiration when drug delivery is delayed and/or drugs have a short lifespan. It is further a feature to prevent delivery of expired drugs.

The tracking computer further assigns a unique package identification number to the dispensing order and the matching of (c) also matches unique package identification number between the dispensing order and completion order.

It is thus a feature of at least one embodiment of the invention to prevent duplicate drug packages in the delivery chain and prevent drug expiration.

The dispensing order and completion order also indicate a patient identity and the matching of (c) also matches patient identity between the dispensing order and completion order.

It is thus a feature of at least one embodiment of the invention to prevent delivering the wrong drug to the wrong patient.

The dispensing terminal pump and tracking computer intercommunicate on an electronic network.

It is thus a feature of at least one embodiment of the invention to provide instantaneous communication with the wireless network for real time updating of drug delivery information.

The dispensing terminal further receives information related to a return of drug for reuse or disposal after drug delivery and the tracking computer communicates with the dispensing terminal to receive the information related to the return of drug.

It is thus a feature of at least one embodiment of the invention to track administration of drugs when network communication is unavailable. It is a further feature to track excess or unused drugs after delivery.

The present invention further provides a system for tracking delivery of medicine to a patient having a dispensing terminal for receiving information from an individual dispensing drugs to create a dispensing order indicating a patient identity, a drug identity and a drug dose for transmission to a medical device; at least one medical device receiving the dispensing order and a completion order identifying the drug delivered to the patient and an amount of drugs delivered to the patient; a tracking computer communicating with dispensing terminals and pumps and executing a program fixed in a non-transitory media to: (a) receive from the dispensing terminal the dispensing order for a given drug; (b) receive at the medical device the completion order for the given drug; (c) compare the dispensing order and the completion order to determine a utilization of the drug providing a comparison between an amount of drug dispensed as indicated by the dispensing order and an amount of drug consumed as indicated by the completion order; and (d) produce a report indicating drug utilization.

It is thus a feature of at least one embodiment of the invention to allow for non-pump delivery of drugs to be recorded into the lifecycle tracking by input of the user, manually, scanned or through wireless communication.

These particular objects and advantages may apply to only some embodiments falling within the claims and thus do not define the scope of the invention.

BRIEF DESCRIPTION OF THE DRAWINGS

FIG. 6 is a logical diagram of a display or database providing a manifest showing the status of drugs during their lifecycle; and FIG. 7 is a representation of a physician report providing information from the manifest including utilization rates of drug on a per physician basis.

DETAILED DESCRIPTION OF THE PREFERRED EMBODIMENT

Figures 1, 4:
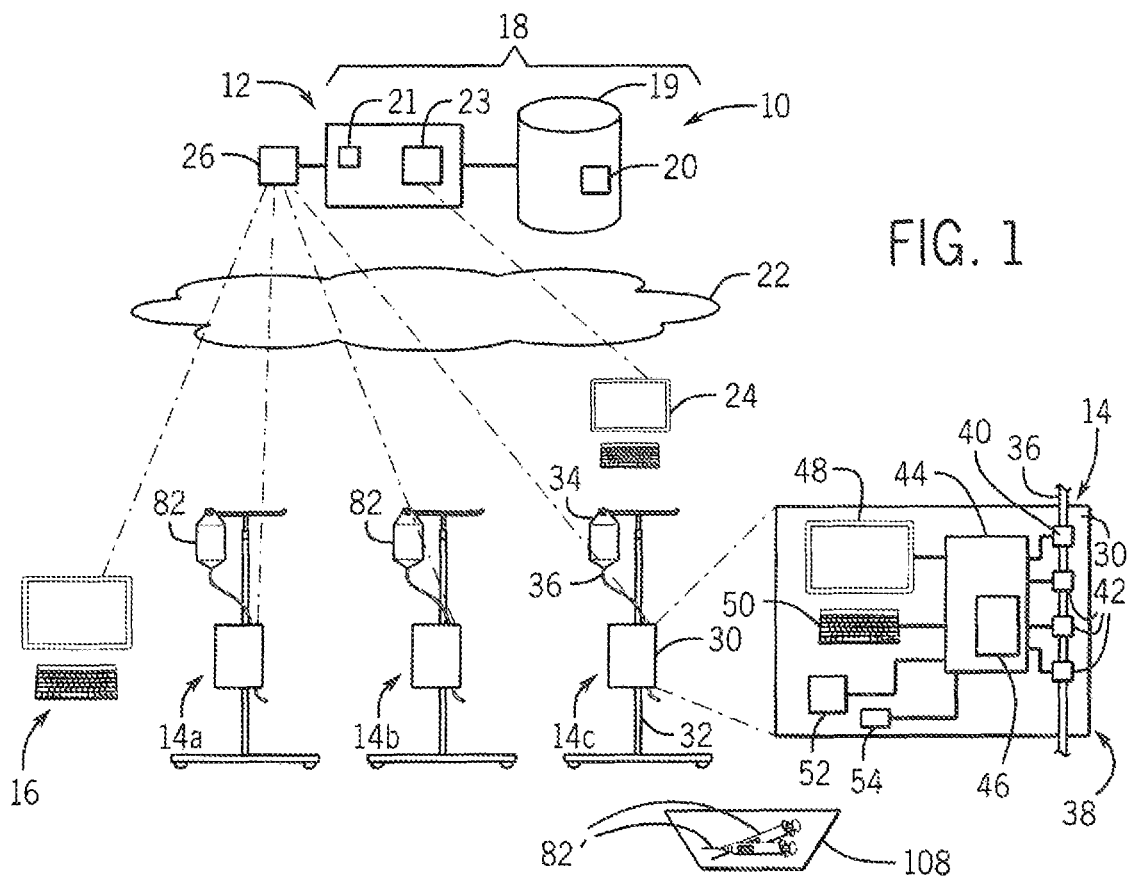
FIG. 1 is a block diagram of a medical pump system per the present invention providing communication between medical pumps and a medical database server showing various functional elements of the pump including an electronic controller executing a control program.
FIG. 4 a depiction of the dispensing of a drug using a medical pump having a bar code reader being one method of validating the set-up of the remotely loaded pump and providing an administration record of the drug as pumped or as manually administered drugs in the vicinity of the pump.

Referring now to FIG. 1, a drug delivery monitoring system 10 of the present invention may provide a file server 12, one or more medical infusion pumps 14a-14c, multiple workstations 16 or dispensing terminals including one at a pharmacy location, all inter-communicating over a wired or wireless network. Note that pumps 14 and workstations 16 can be devices with user interface and communication capability, such as a tablet computer, or other devices suitable for data input, output, storage, and transferring. Such devices can also include authentication capabilities so only authorized personnel can operate them.

The file server 12 may be part of a standard hospital electronic medical record system or may be freestanding and may include a memory system 19, for example, providing a disk array or the like. The memory system 19 may provide part of an electronic medical database 18 holding medical information and patient records and may include a drug dispensary database table 20 providing a listing of drugs and medical pump parameters for the delivery of those drugs to patients as linked to particular patient names for identification as well as drug compounding information.

It will be understood that the database 18 provides both file structures on physical non-transient medium and also a program or database engine for accessing that data according to query instructions. In this regard, the database 18 may provide for a standard database interface, for example, using standard query language or a standardized API, and may further provide an interface accessible over a network. In one embodiment, the network interface may allow communication with the standard database interface using standard network interface conventions, for example, as may be implemented under HTML, XML or other well-known standards. The database engine and portions of the database 18 may be implemented by an electronic computer 21 being part of the file server 12 executing a stored program 23 fixed on physical non-transient medium contained therein.

The server 12 may communicate with a wireless network circuit 26 or the like that may implement a portion of a network 22, for example, providing standard wireless communication protocols such as IEEE 802.11 (a)(b)/(g)/(n). The wireless network card may in turn communicate with corresponding wireless circuitry in each of the medical pumps 14a-14c. The network 22 may also include physical media such as optical or electrical conductors communicating with workstation 16. Such workstations 16, as is understood in the art, may access the database 18 through a standard browser program to generate search queries and to receive query responses that may be used to extract particular information from the database 18. Such file server systems 12 are normally pre-existing in a hospital environment as is necessary for the efficient management of patient information and hospital records independent of the present invention.

Referring still to FIG. 1, each medical pump 14 may provide, for example, a housing 30 that may be releasably attached to a pole 32, the latter of which may support one or more bags of fluid 34 thereupon. The fluid 34 may be a saline solution or any of a number of administered medicines. A tube 36 may pass from the bag through a pump section 38 of the housing 30 of the pump 14 to be received by a peristaltic pump element 40 and one or more sensors 42, for example, including sensors for pressure of the fluid, flow rate of the fluid, air inclusion within the fluid, proper seating of the tube, and the like, all generally understood in the art.

The IV tube 36 may then pass out of the pump section 38 to a needle assembly or catheter (not shown) for attachment to a patient.

Each of the pump element 40 and sensors 42 may connect to an internal controller 44 and execute a stored program 46 fixed on physical non-transient medium to provide control of the pump element 40 according to the program 46 and according to the readings of the sensors 42. The controller 44 may also communicate with user interface elements including a display 48 and a keypad 50 or the like, the latter of which includes communication provided by membrane switches, a touchscreen, or the like. In addition, the controller 44 may communicate with a wireless network circuit 52 similar to the wireless network circuit 26 described above for communication over the network 22. In addition the controller 44 may communicate with a near field communication interface 54 being broadly defined as a reader that requires the read item to be proximate to the pump 14. Near field communication interfaces include data carrier readers, RFID interrogators, and the like.

In an alternative embodiment, one or more of the medical pumps 14 may be a "syringe pump" or an ambulatory pump having similar features to the infusion pump described above, for the introduction of medicines and the like.

Figure 2:
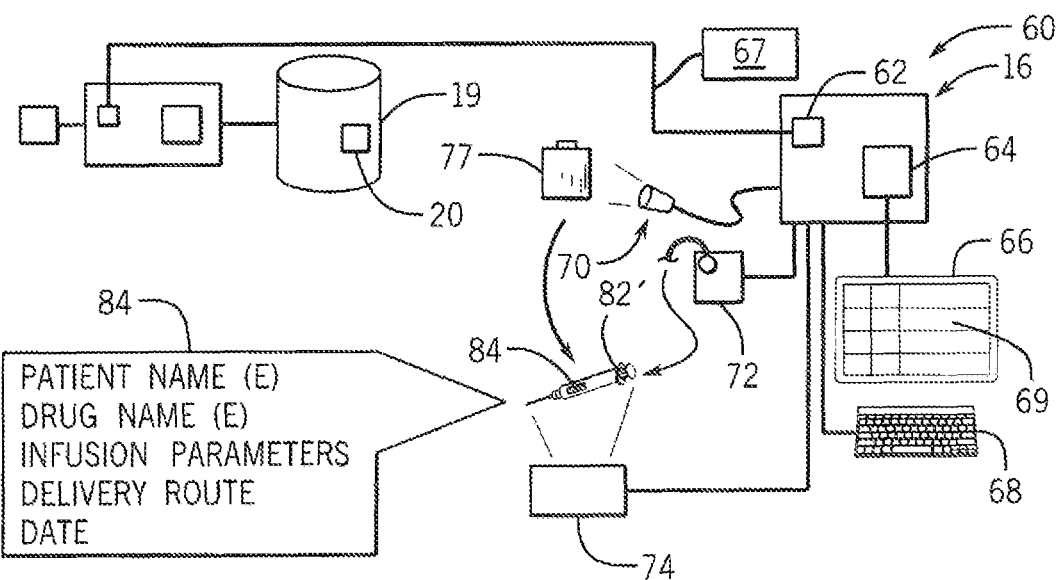
FIG. 2 is a workflow diagram showing the tagging of medicines by a pharmacist at the beginning of a lifecycle tracking of the medicines.

Referring now to FIG. 2, tracking the lifecycle of drugs may begin at the dispensing pharmacy 60 which may communicate with the server 12 as discussed above by a computer workstation 16. Computer workstation 16 may also include a processor 62 running a stored program 64 wherein the processor 62 executes the stored program fixed on physical non-transient medium as will be discussed below. The computer workstation 16 may communicate with a display 66 providing information to the pharmacist and allowing a schedule of all dispensed drugs to be tracked as will be discussed below. A keyboard and cursor control comprising a user interface 68 may provide for user input as will be discussed. In addition computer workstation 16 includes a near field communication interface 70, in this case shown as a barcode scanner, as well as a special label printer 72 as will be discussed below and a drug composition scanner 74.

Figure 3:
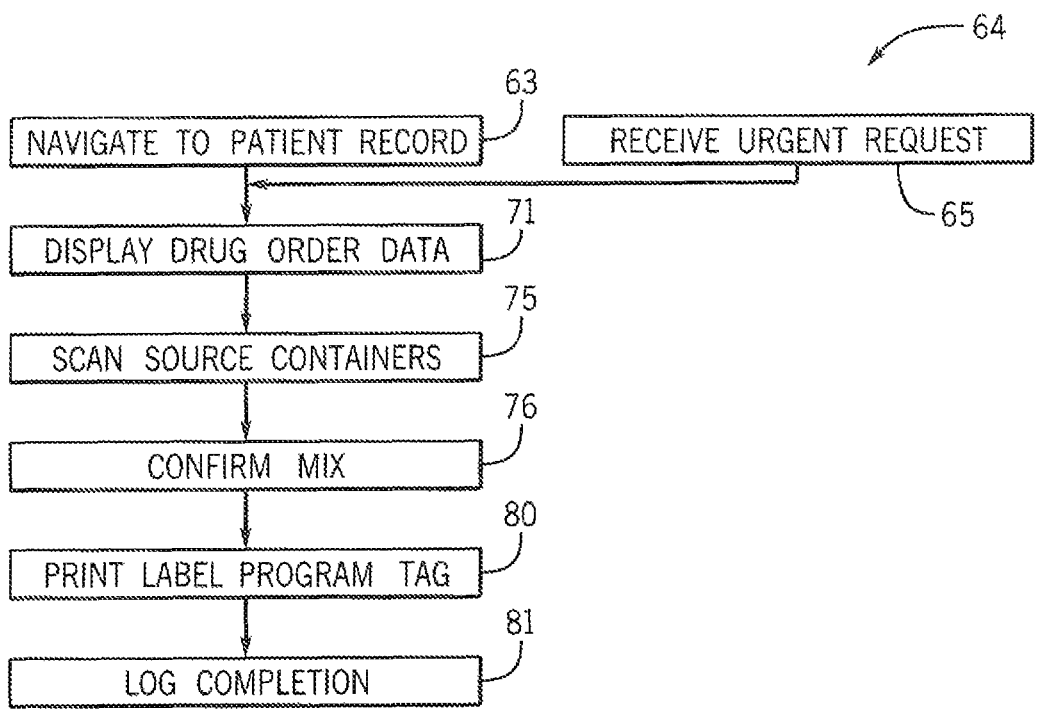
FIG. 3 is a flowchart showing those steps of FIG. 2 implemented by an executed program at a pharmacy workstation.

Referring also to FIG. 3, the pharmacist may interact with the computer workstation 16 at process block 63 by navigating to a particular patient record in database 18 to obtain information about a drug order 67 for that patient (indicating drugs that need to be dispensed for the patient) or to obtain a manifest of open orders that need to be filled. One embodiment of the navigating process is to query database with patient identification number, or part of the patient identification number. The identification number can be manually input by the pharmacist, or through other means such as a scanner. The patient identification number can also be imported from other devices. In addition the pharmacist may receive one or more push notification orders 67 as indicated by process block 65 representing rush orders for medicines. By providing this avenue for rush ordering, it is intended to allow all orders to be processed and logged in the dispensing of the orders by the pharmacist as a part of the tracking system.

Referring momentarily to FIG. 6, the order 67 may be, for example, generated by an attending physician and upon such generation may automatically open a blank record in a drug lifecycle tracking manifest 69 that will be used to track the lifecycle of dispensed drug indexed by an order number 73 that will be unique to each order over an indefinitely long period of time (e.g., for many years). An identity of the prescribing physician may be linked to each order 67 for later association with a utilization rate for each order 67.

Referring again also to FIG. 3, at process block 71 the date of the drug order 67 for the patient may be provided on the display 66 indicating the patient and drug type, providing detailed instructions for any compounding necessary by the pharmacist, for example, in the mixing of different drug types and information about drug interaction or the like. As part of providing mix information, the display at process block 71 may show an interactive recipe allowing the pharmacist to check each step as it is complete. Alternatively, electronic information may be provided to automatic mixing or compounding equipment.

The pharmacist may modify or supplement the data of this drug order 67 based on the pharmacist's knowledge or may augment the data, for example, by selecting a particular brand name of drug required and whether the drug will be delivered in separate packages or as a mixed drug in a single package 82. As used herein, package 82 should be understood to be any sort of container for medicines including a pouch, syringe, or bag or the like. Information about modifications or supplementation of the drug order 67 by the pharmacist may be entered into the user interface 68, for example, as notes 78 and will form part of the drug lifecycle tracking manifest 69.

At process block 75, the source containers 77 from which the drug will be repackaged or compounded (for example, as delivered from the pharmaceutical company) may be marked with identifying information including drug name, lot number, and unique package serial numbers and may be scanned by the interface 70 to help confirm that the proper source materials are used for the drug preparation for the patient. In the scanning process, a remaining weight or amount of the drug in the container 77 may be noted for the purpose of reordering or tracking the material of the container 77. If the scanned container 77, for example, by reading a data carrier or RFID tag, does not match with the drug order 67 obtained from the server, an error may be noted to the pharmacist and recorded in the drug tracking manifest to prevent incorrect medicines from being delivered to the patient.

After the dispensing or compounding process is complete, at process block 76 the system allows the prepared drug to be verified, for example, by scanner 74 which may make use of spectroscopic scanning to confirm concentrations of the drug or a signature consistent with the desired compounding. The scanner 74 may also weigh the drug and that weight may be netted by knowledge of the empty weight of the drug package 82.

At process block 80, a tag 84 may be printed for the package 82 into which the drug has been dispensed and placed on the package 82. This tag 84 may include the information of the prescribing physician name, patient name, drug name, infusion parameters (for example, dose delivery rate and amount or dose of drug to be delivered), a delivery route (for example, intravenously through the arm) and the date of the dispensing as well as a date of expiration of the drug indicating how long dispensed drug may be held before use. Storage requirements may also be included, for example, temperatures, and the like. The tag 84 may be tamper resistance or tamper proof to prevent tampering of the tag 84 after the tag 84 is affixed to the package 82.

Any or all of this data may be encrypted or encoded or provided in duplicate human readable and machine readable form, these processes, for example, providing a data carrier or other optically scanned coding system and may thereby provide privacy, machine readability, and tamper resistance as desired. It will be understood that the tag 84 may likewise include both the printed and RFID or other electronically readable tag medium and that the encoding may operate to encode information in the RFID tag (thus serving as the encoding) or may be further encrypted before encoded in the RFID tag.

At process block 81, once the medicine is ready to be delivered to the patient from the pharmacy, dispensing information is entered into the drug lifecycle tracking manifest 69 to clearly indicate that a dispensing has occurred and when the dispensing occurred as well as the particular amounts and drug of the dispensing as well as the source containers 77 and indications of the identity of the authorized pharmacist. At the time of dispensing, a unique package ID 83 is assigned to the package 82 so that it may be tracked in the drug lifecycle tracking manifest 69. This unique package ID 83 may also be encoded in the tag 84.

At block 81, the status of the drug as "dispensed" per column 86 may be recorded (changed from "pending" to a dispensing date and time). This column 86 is initialized at the time of generation of the order 67 as "pending" for orders 67 retrieved by the pharmacist and as "urgent" for push orders 67 to allow a sorting by the pharmacist to attend to urgent dispensing requirements in priority. A patient name may be entered into column 88 and other information may be entered into column 89, including drug dose and any or all of the information on the tag 84, automatically from the order 67.

Figure 5:
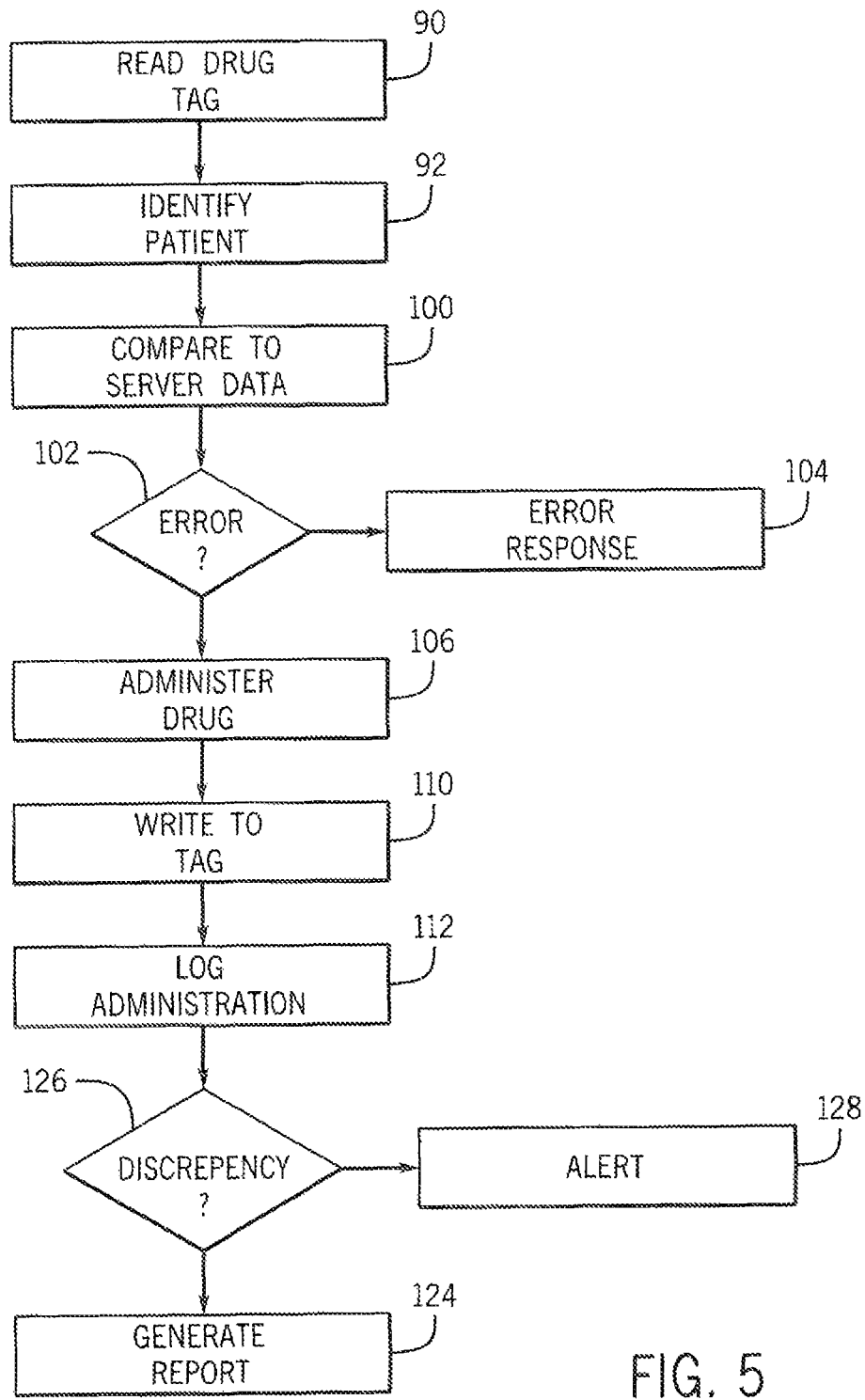
FIG. 5 is a flowchart showing the steps implemented with respect to FIG. 4 implemented by an executed program on a pump.

Referring now to FIGS. 1, 4 and 5, the drug package 82 may then be delivered to a healthcare professional to be attached to the pump 14 for delivery. The tag 84 will be readily accessible on the package 82.

As indicated by process block 90 of FIG. 5, the program 46 of the pump controller may instruct the healthcare professional to read the tag for guidance with respect to administering the drug of the package 82 and this information may be scanned from the tag 84 using the near field communication interface 54, in this case shown as a data carrier scanner but also may be an RFID scanner or the like, and displayed on the display 48 (shown in FIG. 1) of the pump for this purpose. This information may also automatically be read into the pump 14 for use as will be described below.

At process block 92, the healthcare professional may be instructed to scan a wrist tag 96 on the patient 98 with the near field communication interface 54 to obtain patient information to confirm the correct patient is receiving the drug, or this information may be manually entered by the healthcare professional. The healthcare professional may be further instructed to scan the tag 84 on the drug package 82 with the near field communication interface 54 to obtain drug information to confirm that the patient is receiving the correct drug. The function of the near field communication interface 54 may be implemented by a portable wireless device such as an iPhone or Android phone or similar smart device having a camera or similar element that may be used to read the data carrier, decode the data carrier, and forward the information to the pump 14 by near field communication, but may also be by Bluetooth, infrared channel or the like. In addition, the near field communication interface 54 may be used to scan the pump 14 itself. In this way, these devices may also be used to positively identify the pump 14 and the drug, as well as the patient, and to allow activation of the pump 14 only if the patient, pump 14, and drug matches the original order 67 and/or the drug lifecycle tracking manifest 69. Clearly, the near field communication interface 54 may be replaced with other local scanning devices including RFID tags and a reader, or the like. The near field communication interface 54 may be implemented as a wireless device and the scanning operation can be performed using a portable device such as a tablet computer, smartphone or the like.

The pump 14 may communicate with the server 12 holding the original order 67 and/or the drug lifecycle tracking manifest 69 to match the patient identification from the wrist tag 96 and information from the tag 84 as indicated by process block 100. This matching may confirm not only that the patient name and drug name are correct but also that the unique package ID 83 is correct (addressing the problem of possible duplicate drug packages in the delivery chain) and that the drug has not expired at a time proximate to the start of drug delivery.

Any error detected at process block 102 will result in an error response 104, for example, a refusal to pump 14 or to dispense the drug, and a notification to the healthcare professional. The display 48 on the pump 14 may also provide other instructions to the healthcare professional from the tag 84 or from the server 12, for example, confirming information about the patient and drug name as well as the delivery route information and may receive information from the healthcare professional, for example, a confirmation of infusion parameters controlling the pump 14 (for example, dose amount and dose rate) that can be obtained automatically from the server 12 and/or tag 84 for programming the pump 14. By providing duplicate information from the server 12 and on tag 84, additional redundancy against error is provided and the ability to operate the pump with these safeguards in the event of a network outage is also provided.

As indicated by process block 106, the drug may then be administered by the pump 14. The pump 14 may alternatively provide for a recording of non-pump delivered medicaments, for example, from a package 82' used in an operating room and administered manually. The pump 14 may be associated with a collection basket 108 located to be scannable by the near field communication interface 54 to allow a convenient mechanism for use in an operating room or the like for manually administered drugs to be brought into the drug lifecycle tracking manifest 69 of the present invention.

The administration of drugs by the pump 14 may be monitored to record delivery data by the pump 14. For example, the pump 14 may monitor and record an amount of drug dispensed by the pump 14, such as may prevent a user from dispensing less than the drug dose to be delivered to the patient and carried by the package 82. The pump 14 may also monitor and record whether the delivery of drugs was interrupted during administration, either through mechanical failure or intervention by an individual operating the pump 14. Complete delivery of the drug by the pump 14 may be indicated by a discontinuation in drug delivery for a predetermined amount of time, disconnection of the package 82 from the pump 14, or as manually indicated by the user.

An example pump suitable for use with the present invention is described in U.S. Pat. No. 8,652,093, entitled System for Programming Medical Pumps with Reduced-Error, U.S. Pat. No. 8,945,043, entitled Medical Device with Contextual Awareness, U.S. Pat. No. 9,378,334, entitled Medical Pump Providing Customizable Programming Permissions, US patent, US patent application 2015/0165118, entitled Medical Pump with Operator Authorization Awareness, and US patent application 2014/0194817, entitled Medical Pump with Operator-Authorization Awareness, all of which are all hereby incorporated by reference.

Referring again to FIGS. 5 and 6, after administration of the drug per process block 106, a tag 84 including writable elements such as a writable RFID tag may be written to by the pump 14 to indicate that the drug has been dispensed from the package 82, including, for example, a date (denoting time and/or date) of the dispensing, such as may prevent reuse of the package 82 as indicated by process block 110. This writing process may also be part of a package return tracking system where the package 82 is then returned to the pharmacy for verification and may provide an indication that the drug has been administered even in the absence of server connection. The package return tracking system may report to the server 12 a date of package return to the pharmacy, provided by drug return column 130, where an amount of drug remaining in the returned package 82, provided by amount returned column 132, is also reported to the server 12 to account for drug amounts that were not delivered to the patient during drug delivery and to account for discrepancies in the drug delivery. The drug package 82 may be weighed and netted by knowledge of the empty weight of the drug package 82 to determine a leftover drug weight, for example, by scanner 74.

Per process block 112, the administration of the drug may be reported to the server 12 and recorded to the drug lifecycle tracking manifest 69 provided in an administration column 114 a time of administration of the drug. This column 114 may also indicate an expiration rather than administration if administration of the drug is not performed before the expiration time of the drug. A utilization (e.g., rate or percentage) may be recorded to the server 12 to complete the drug lifecycle tracking manifest 69 to provide a comparison of the dose amount prescribed by the physician to what was actually delivered to the patient as provided in utilization rate column 120.

Per process block 126, if an error is detected, an automatic alert 128 may alert the medical professional to the discrepancy or error. An amount of drug delivered may be reported to the server 12 and provided in an amount delivered column 118. An alert 128 may be produced if the amount of drug delivered differs from the drug dose entered by the pharmacist into the drug lifecycle tracking manifest 69 by more than a predetermined amount at the conclusion of delivery, as noted above. The alert 128 allows the medical professional to immediately investigate the cause of the discrepancy before the patient leaves the drug delivery site. The alert 128 may for example be displayed on administrative terminal or the like or emailed to individuals if it is desired to have the ability for short-term response. The alert 128 may also be a visual or audible alarm. Otherwise it may be noted in a report as described below. Finally, whether the delivery of drugs was interrupted as indicated by the pump 14 may be indicated in an interruption column 122. An alert 128 may be produced if the delivery of drugs is interrupted, as indicated by the pump 14 so that a medical professional may investigate the cause of the interruption and correct the interrupted state. Otherwise it may be noted in a report as described below.

An optional status column 116 may be provided that summarizes the current status of the drug order 67 collecting information from the dispensing column 86 and the administration column 114 and allows rapid sorting of the information of the drug lifecycle tracking manifest 69 as desired.

Per process block 124, a report may be generated providing an output of the drug lifecycle tracking manifest 69 including any number of columns 73, 83, 88, 86, 114, 118, 120, 122, 116, and 78 as desired, for example, on a computer screen, monitor, or a print out. The report may include other information reported to or recorded to the server 12, for example the alert 128 may be recorded under the notes 78 column.

A physician report 134 may also be produced to provide unique information for each individual prescribing physician 142. The utilization of a prescribed drug may be linked to the physician prescribing the drug order 67 to allow the physician to view, for example, the order number 73, unique package ID 83, and utilization 120 for all of the prescribing physician's completed orders. The physician's report 134 may include any other information or notes 78 also recorded to lifecycle tracking manifest 69. An average utilization 136 may be recorded to the physician report 134 providing a comparison of average utilization rates between physicians, hospital departments, or hospitals. The report 134 may also be broken down by drug type, e.g., controlled substances 138 and uncontrolled substances 140.

It will be appreciated that the system of the present invention, by assigning a unique package ID 83 to each dispensed drug and enlisting the pumps 14 to record administration of drugs (manual or automatic), provides improved tracking of drug usage and provides a mechanism for reducing waste and preventing duplicate orders and may reduce improper misdirection of drugs in a hospital environment or the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

We claim:

1. A system for tracking delivery of medicine in a drug delivery container comprising:
  a dispensing terminal for receiving information from an individual dispensing drugs to create a dispensing order indicating the drug identity, an intended drug dose, and an intended delivery rate for transmission to at least one electronic computer-controlled infusion pump;
  the at least one electronic computer-controlled infusion pump comprising:
    a data carrier reader receiving a drug identification from a drug data carrier, the drug data carrier affixed to the external IV bag and tamper resistant;
    a housing holding
      an IV line support structure receiving an IV line set communicating between an external IV bag and a patient connection;
    a user interface providing a display and a keypad;
    a sensor configured to measure at least one of a pressure of the drug, flow rate of the drug, air inclusion within the IV line, and proper seating of the IV line;
    a peristaltic pump element configured to control the flow of fluid through an IV line when the IV line is held in the IV line support structure;
    an electronic computer communicating with the peristaltic pump element and the user interface and executing a program stored in a non-transitory computer readable storage medium to:
      (1) receive the dispensing order to administer a drug to a patient according to the dispensing order including the intended drug dose and intended delivery rate;
      (2) control operation of the peristaltic pump element based on the drug dose and intended delivery rate;
      (3) measure an amount of drugs infused by the peristaltic pump element indicating an amount of drug administered to the patient independent of the intended drug dose;
      (4) detect a combination of a drug interruption in the peristaltic pump element operation after a start of drug delivery followed by a continued drug delivery to a completion of drug delivery; and
      (5) transmit a completion order identifying the measured amount of drug infused by the peristaltic pump element identifiable to the drug identity and whether the delivery of drugs was interrupted in the course of drug delivery, following the completion of drug delivery; and
  a tracking computer communicating with the dispensing terminals and the at least one electronic computer-controlled infusion pump and executing a program fixed in a non-transitory media to:
    (a) receive the dispensing order for a given drug;
    (b) receive the completion order for the given drug;
    (c) match the completion order to the dispensing order to determine utilization of the given drug providing a comparison between the intended drug dose as indicated by the dispensing order and the measured amount of drug infused by the computer-controlled infusion pump as indicated by the completion order and further providing an indication of a discrepancy between drug administered to the patient and the intended drug dose and whether drug administration is interrupted;
    (d) generate a real time alert at the time of completion of drug delivery when the intended drug dose is fully delivered and when there is a discrepancy following the completion of drug delivery between drug administered to the patient and the intended drug dose; and
    (e) generate a real time alert at the time when the intended drug dose is fully delivered and when the combination of the drug delivery interruption after the start of drug delivery followed by the continued drug delivery to the completion of drug delivery is detected.

2. The system of claim 1 wherein the tracking computer produces an alert when the utilization is below a predetermined threshold value.

3. The system of claim 1 wherein the dispensing order also includes a physician identification and the tracking computer communicating with the pump outputs a physician report indicating drug utilization on a physician basis.

4. The system of claim 1 wherein the data carrier reader matches the drug identification with the dispensing order.

5. The system of claim 4 wherein operation of the pump is allowed only if patient and drug information entered into the pump is consistent with the dispensing order.

6. The system of claim 4 wherein the pump data carrier reader receives a patient identification from a patient data carrier and matches the patient identification with the dispensing order.

7. The system of claim 1 wherein the pump transmits a date of drug administration of the given drug and the tracking computer communicating with the pump receives the date of drug administration to output the lifecycle report indicating a date of drug administration of the given drug.

8. The system of claim 1 wherein the dispensing order includes a drug expiration date and the tracking computer matches the expiration date with a date at a start of drug administration to determine a drug expiration status.

9. The system of claim 1 wherein the tracking computer further assigns a unique package identification number to the dispensing order and the comparing of (c) also compares unique package identification number between the dispensing order and completion order.

10. The system of claim 1 wherein the dispensing order and completion order also indicate a patient identity and the comparing of (c) also compares patient identity between the dispensing order and completion order.

11. The system of claim 1 wherein the at least one electronic computer-controlled infusion pump and tracking computer intercommunicate on an electronic network.

12. The system of claim 1 wherein the tracking computer communicates with the dispensing terminal to receive information related to a return of leftover drug.

13. A system for tracking delivery of medicine to a patient comprising:
 a dispensing terminal for receiving information from an individual dispensing drugs to create a dispensing order indicating a patient identity, a drug identity, an intended drug dose, and an intended delivery rate for transmission to at least one electronic computer-controlled infusion pump;
 the at least one electronic computer-controlled infusion pump comprising:
  a housing holding
   an IV line support structure receiving an IV line set communicating between an external IV bag and a patient connection;
   a user interface providing a display and a keypad;
   a sensor configured to measure at least one of a pressure of the drug, flow rate of the drug, air inclusion within the IV line, and proper seating of the IV line;
   a peristaltic pump element to control the flow of fluid through an IV line when the IV line is held in the IV line support structure;
   an electronic computer communicating with the peristaltic pump element and the user interface and executing a program stored in a non-transitory computer readable storage medium to:
   (1) receive the dispensing order to administer a drug to a patient according to the dispensing order including the intended drug dose and intended delivery rate;
   (2) control operation of the peristaltic pump element based on the drug dose and intended delivery rate;
   (3) measure an amount of drugs infused by the peristaltic pump element indicating an amount of drug administered to the patient independent of the intended drug dose;
   (4) detect a combination of a drug interruption in the peristaltic pump element operation after a start of drug delivery followed by a continued drug delivery to a completion of drug delivery; and
   (5) transmit a completion order identifying the measured amount of drug infused by the peristaltic pump element identifiable to the drug identity and whether the delivery of drugs was interrupted in the course of drug delivery, following the completion of drug delivery; and
  a data carrier reader receiving a drug identification from a drug data carrier, the drug data carrier affixed to the external IV bag and tamper resistant:
 a tracking computer communicating with dispensing terminals and the at least one electronic computer-controlled infusion pump and executing a program fixed in a non-transitory media to:
  (a) receive from the dispensing terminal the dispensing order for a given drug;
  (b) receive at the at least one electronic computer-controlled infusion pump the completion order for the given drug;
  (c) compare the dispensing order and the completion order to determine a utilization of the drug providing a comparison between an intended drug dose as indicated by the dispensing order and the measured amount of drug infused as indicated by the completion order and further providing an indication of a discrepancy between a drug administered to the patient and the intended drug dose and whether drug administration is interrupted;
  (d) generate a real time alert at the time of completion of drug delivery when the intended drug dose is fully delivered when there is a discrepancy following the completion of drug delivery between drug administered to the patient and the intended drug dose; and
  (e) generate a real time alert at the time when the intended drug dose is fully delivered when the combination of the drug delivery interruption after the start of drug delivery followed by the continued drug delivery to the completion of drug delivery is detected.

14. The system of claim 13 wherein the dispensing order indicates a unique package identification number and the completion order identifies the unique package identification number of an administered drug and the comparing of (c) also compares unique package identification number between the dispensing order and completion order.

15. The system of claim 13 wherein the dispensing order and completion order also indicate a patient identity and the comparing of (c) also compares patient identity between the dispensing order and completion order.

16. The system of claim 15 wherein the tracking computer produces an alert when the patient identity of the dispensing order and the completion order do not match.

17. The system of claim 13 wherein the tracking computer receives information related to a return of drugs for reuse or disposal after drug administration.

18. The system of claim 1 wherein the completion of drug delivery is indicated by a predetermined amount of time.

19. The system of claim 1 wherein the completion of drug delivery is indicated by a disconnection of the IV line set from the at least one electronic computer-controlled infusion pump.

20. The system of claim 1 wherein the completion of drug delivery is indicated by a manual indication by the user.

\* \* \* \* \*